United States Patent [19]
Takahashi et al.

[11] Patent Number: 6,150,363
[45] Date of Patent: Nov. 21, 2000

[54] DIHYDROPHENAZINECARBOXYLIC ACID DERIVATIVES

[75] Inventors: Toshihiro Takahashi, Misato; Yutaka Nomura, Noda; Haruo Seto, Hachioji; Kazuo Shin-ya, Tokyo, all of Japan

[73] Assignee: Nippon Chemiphar Co., Ltd., Tokyo, Japan

[21] Appl. No.: 09/319,285

[22] PCT Filed: Oct. 14, 1997

[86] PCT No.: PCT/JP97/03674

§ 371 Date: Jun. 2, 1999

§ 102(e) Date: Jun. 2, 1999

[87] PCT Pub. No.: WO98/24772

PCT Pub. Date: Jun. 11, 1998

[30] Foreign Application Priority Data

Dec. 3, 1996 [JP] Japan .................................. 8-337492

[51] Int. Cl.[7] ...................... A61K 31/495; C07D 241/46
[52] U.S. Cl. ............................................ 514/250; 544/347
[58] Field of Search ...................... 544/347, 250

[56] References Cited

U.S. PATENT DOCUMENTS

| | | | |
|---|---|---|---|
| 1,886,365 | 11/1932 | Bayer et al. | 544/347 |
| 3,080,283 | 3/1963 | Bijloo et al. | 544/347 |
| 3,752,813 | 8/1973 | Shen et al. | 544/347 |
| 4,593,097 | 6/1986 | Tomita et al. | 544/347 |

*Primary Examiner*—Deborah C. Lambkin
*Attorney, Agent, or Firm*—Reed Smith Shaw & McClay LLP

[57] ABSTRACT

Dihydrophenazinecarboxylic acid derivatives of the formula (I) wherein $R^1$ represents hydrogen, linear or branched alkyl, etc., each of $R^2$ and $R^3$ represents hydrogen, 3-methyl-2-butenyl, etc., and each of $R^4$ and $R^5$ represents hydrogen, alkyl, alkenyl, aralkyl, aryl, hydroxyl, alkoxy, aryloxy, aralkyloxy, halogen, nitro, cyano, alkylsulfonyl, arylsulfonyl, alkylcarbonyl, arylcarbonyl, etc., provided that there is no case that both of $R^4$ and $R^5$ are hydrogen. The dihydrophenazinecarboxylic acid derivatives are excellent in the inhibition of glutamic acid toxicity.

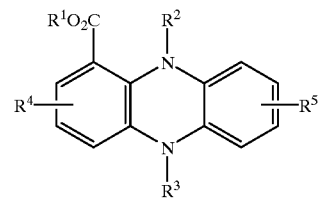

6 Claims, No Drawings

DIHYDROPHENAZINECARBOXYLIC ACID DERIVATIVES

This application is a 371 of PCT/P97/03674 Oct. 14, 1997.

FIELD OF THE INVENTION

This invention relates to dihydrophenazinecarboxylic acid derivatives. More particularly, the invention relates to dihydrophenazinecarboxylic acid derivatives having the below-mentioned formula (I) or (III), and an inhibitory agent of glutamic acid toxicity which contains a dihydrophenazinecarboxylic acid derivative having the below-mentioned formula (I), (III) or (V) as an active ingredient.

BACKGROUND OF THE INVENTION

It is known that glutamic acid which is one of natural amino acids has toxicity to neurocyte (Akaike Akinori, Folia Pharmacol. Jpn. 103, 193–201 (1994), etc.). A substance inhibiting glutamic acid toxicity to neurocyte is employable as a brain metabolism activating agent or a brain metabolism improving agent.

Seto et al. reported that sugar moiety-containing dihydrophenazinecarboxylic acid derivatives represented by the below-mentioned formulas (A) and (B) [aestivophoenins A & B] which were isolated from actinomyces belonging to genus Streptomyces inhibit glutamic acid toxicity and shows antioxidant property: J. Antibiotics, 48, 1378 (1995) and PCT WO96/22996.

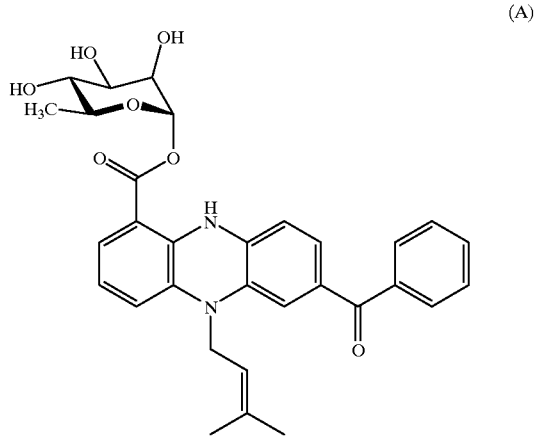

(A)

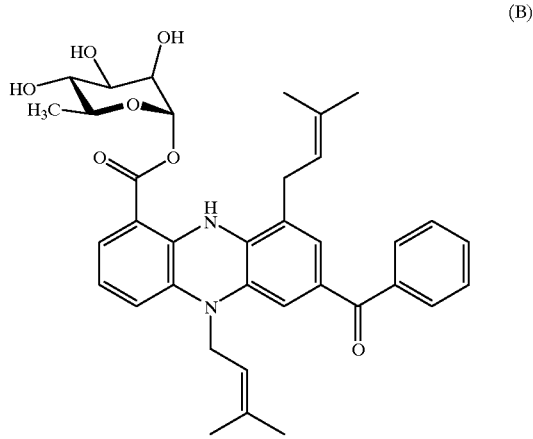

(B)

Further, a dihydrophenazinecarboxylic acid derivative having no sugar moiety which is represented by the following formula (C):

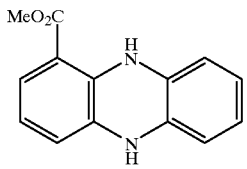

is known {Ann. Chim. [13], 1, 115(1956)].

Also known is a compound of the following formula (D) which has no sugar moiety (benthophoenin):

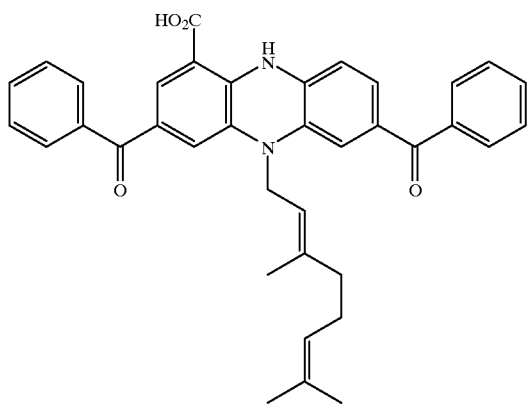

and its methyl ester. These compounds are reported to be employable as a free radical scavenger (anti-oxidant). [J. Nat. Prod., 56, 1255(1993)].

Also known is a compound of the following formula (E) which has no sugar moiety:

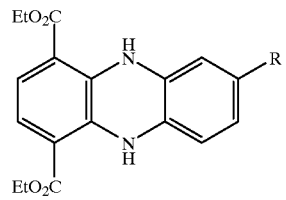

wherein R represents hydrogen, methyl or nitro [Helv. Chim. Acta, 52, 322(1969)].

Also known is a compound of the following formula (F) which has no sugar moiety:

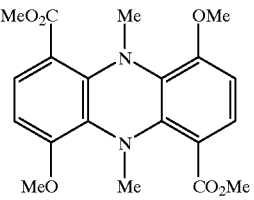

[J. Gen. Microbiol., 104, 299(1978)].

As for the above-mentioned dihydrophenazinecarboxylic acid derivatives having no sugar moiety, the publications give no description concerning inhibition of glutamic acid toxicity.

The compound having the aforementioned formula (D) is obtained only from the mycelium of *Streptomyces prunicolor*.

The compounds having the aforementioned formulas (A) and (B) which are reported to show inhibition of glutamic acid toxicity are natural products. It is not expected to produce enough amounts of these compounds by culture. Further, it is difficult to prepare these compounds by organic synthetic methods because the compounds have L-rhamnose residue in the molecular structure. Until now, no reports have been given on total synthesis of these compounds or their analogs.

Accordingly, it is desired to provide dihydrophenazinecarboxylic acid derivatives which show inhibition of glutamic acid toxicity and which are easily synthesized.

DISCLOSURE OF THE INVENTION

The inventors studied on compounds showing inhibition of glutamic acid toxicity and discovered that dihydrophenazinecarboxylic acid derivatives having no sugar moiety and being represented by the under-mentioned formula (I), (III) or (V) shows excellent inhibitory activity against glutamic acid toxicity. The present invention has been made on the discovery.

The present invention resides in a dihydrophenazinecarboxylic acid derivative having the formula (I):

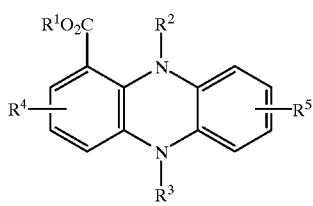

(I)

in which $R^1$ represents a hydrogen atom, a linear or branched chain alkyl group, an aralkyl group or an aryl group;

each of $R^2$ and $R^3$ is the same or different from each other and represents a hydrogen atom, an alkenyl group having 2 to 5 carbon atoms, an alkyl group, an aralkyl group, an aryl group, or a group represented by the formula (II):

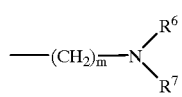

(II)

wherein each of $R^6$ and $R^7$ is the same or different from each other and represents a hydrogen atom, a linear or branched chain alkyl group, an aralkyl group or an aryl group, or $R^6$ and $R^7$ are combined together to form a nitrogen atom-containing 5- to 7-membered ring in conjunction with the adjacent nitrogen atom, and m is 2, 3 or 4;

each of $R^4$ and $R^5$ is the same or different from each other and represents a hydrogen atom, a linear or branched chain alkyl group, an alkenyl group, an alkynyl group, an aralkyl group, an aryl group, a hydroxyl group, an alkoxy group, an aryloxy group, an aralkyloxy group, a halogen atom, a nitro group, a cyano group, an alkylsulfonyl group, an arylsulfonyl group, an alkylcarbonyl group, an arylcarbonyl group, an aralkylcarbonyl group, a halo-alkyl group, a halo-alkoxy group, or a group represented by —$NR^8R^9$ or —$SO_2NR^{10}R^{11}$ wherein each of $R^8$ and $R^9$ is the same or different from each other and represents a hydrogen atom, a linear or branched chain alkyl group, an aralkyl group or an aryl group, and each of $R^{10}$ and $R^{11}$ is the same or different from each other and represents a hydrogen atom, a linear or branched chain alkyl group, an aralkyl group or an aryl group; provided that there is no case that $R^4$ and $R^5$ both are hydrogen atoms.

The invention further resides in a dihydrophenazinecarboxylic acid derivative having the formula (III):

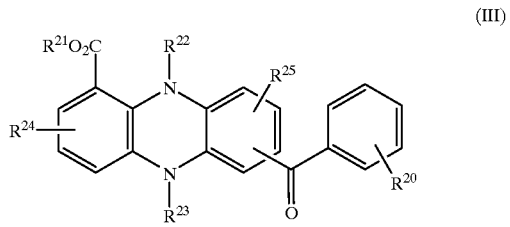

(III)

in which $R^{21}$ represents a hydrogen atom, a linear or branched chain alkyl group, an aralkyl group or an aryl group;

each of $R^{22}$ and $R^{23}$ is the same or different from each other and represents a hydrogen atom, an alkenyl group having 2 to 5 carbon atoms, an alkyl group, an aralkyl group, an aryl group, or a group represented by the formula (IV):

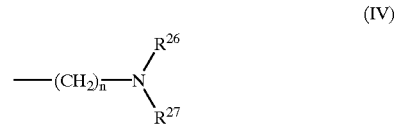

(IV)

wherein each of $R^{26}$ and $R^{27}$ is the same or different from each other and represents a hydrogen atom, a linear or branched chain alkyl group, an aralkyl group or an aryl group, or $R^{26}$ and $R^{27}$ are combined together to form a nitrogen atom-containing 5- to 7-membered ring in conjunction with the adjacent nitrogen atom, and n is 2, 3 or 4;

each of $R^{20}$, $R^{24}$ and $R^{25}$ is the same or different from each other and represents a hydrogen atom, a linear or branched chain alkyl group, an alkenyl group, an alkynyl group, an aralkyl group, an aryl group, a hydroxyl group, an alkoxy group, an aryloxy group, an aralkyloxy group, a halogen atom, a nitro group, a cyano group, an alkylsulfonyl group, an arylsulfonyl group, a halo-alkyl group, a halo-alkoxy group, or a group represented by —$NR^{28}R^{29}$ or —$SO_2NR^{30}R^{31}$ wherein each of $R^{28}$ and $R^{29}$ is the same or different from each other and represents a hydrogen atom, a linear or branched chain alkyl group, an aralkyl group or an aryl group, and each of $R^{30}$ and $R^{31}$ is the same or different from each other and represents a hydrogen atom, a linear or branched chain alkyl group, an aralkyl group or an aryl group.

The invention furthermore resides in an inhibitory agent of of glutamic acid toxicity containing an effective amount of a dihydrophenazinecarboxylic acid derivative of the aforementioned formula (I) or (III) [active ingredient].

The invention furthermore resides in an inhibitory agent for inhibition of glutamic acid toxicity containing an effective amount of a dihydrophenazinecarboxylic acid derivative of the following formula (V):

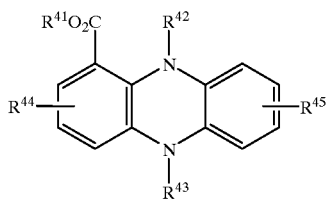

(V)

in which

R[41] represents a hydrogen atom, a linear or branched chain alkyl group, an aralkyl group or an aryl group;

each of R[42] and R[43] is the same or different from each other and represents a hydrogen atom, an alkyl group, an aralkyl group, an aryl group, an alkenyl group having 2 to 5 carbon atoms, or a group represented by the formula (VI):

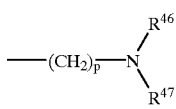

(VI)

wherein each of R[46] and R[47] is the same or different from each other and represents a hydrogen atom, a linear or branched chain alkyl group, an aralkyl group or an aryl group, or R[46] and R[47] are combined together to form a nitrogen atom-containing 5- to 7-membered ring in conjunction with the adjacent nitrogen atom, and p is 2, 3 or 4;

each of R[44] and R[45] is the same or different from each other and represents a hydrogen atom, a linear or branched chain alkyl group, an alkenyl group, an alkynyl group, an aralkyl group, an aryl group, a hydroxyl group, an alkoxy group, an aryloxy group, an aralkyloxy group, a halogen atom, a nitro group, a cyano group, an alkylsulfonyl group, an arylsulfonyl group, an alkylcarbonyl group, an arylcarbonyl group, an aralkylcarbonyl group, a halo-alkyl group, a halo-alkoxy group, a carboxyl group, an alkoxycarbonyl group, an aralkyloxycarbonyl group, a formyl group, or a group represented by —NR[48]R[49] or —SO$_2$NR[50]R[51] wherein each of R[48] and R[49] is the same or different from each other and represents a hydrogen atom, a linear or branched chain alkyl group, an aralkyl group or an aryl group, and each of R[50] and R[51] is the same or different from each other and represents a hydrogen atom, a linear or branched chain alkyl group, an aralkyl group or an aryl group.

PREFERRED EMBODIMENTS OF THE INVENTION

The dihydrophenazinecarboxylic acid derivative of the formula (I) is described in more detail.

In the formula (I), R[1] can be a hydrogen atom, a linear or branched chain alkyl group having 1 to 8 carbon atoms (e.g., methyl, ethyl, propyl, isopropyl, butyl, isobutyl, or tert-butyl), an aralkyl group having an alkylene moiety of 1 to 4 carbon atoms (e.g., benzyl or phenethyl), or an aryl group (e.g., phenyl or naphthyl).

Each of R[2] and R[3] is the same or different from each other and can be a hydrogen atom, an alkenyl group having 2 to 5 carbon atoms (e.g., allyl or 3-methyl-2-butenyl), an alkyl group having 1 to 8 carbon atoms (e.g., methyl, ethyl, propyl, isopropyl, butyl, isobutyl, or tert-butyl), an aralkyl group having an alkylene moiety of 1 to 4 carbon atoms (e.g., benzyl or phenethyl), an aryl group (e.g., phenyl or naphthyl), or a group represented by the formula (II):

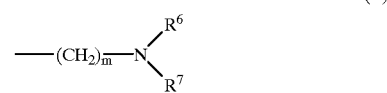

(II)

(wherein each of R[6], R[7] and m has the aforementioned meaning).

In the group represented by the formula (II), each of R[6] and R[7] is the same or different from each other, and can be a hydrogen atom, an alkyl group having 1 to 8 carbon atoms (e.g., methyl, ethyl, propyl, isopropyl, butyl, or isobutyl), an aralkyl group having an alkylene moiety of 1 to 4 carbon atoms (e.g., benzyl or phenethyl), an aryl group (e.g., phenyl or naphthyl). Otherwise, R[6] and R[7] are combined together to form a nitrogen atom-containing 5- to 7-membered ring (e.g., pyrrolidine or piperidine) in conjunction with the nitrogen atom to which R[6] and R[7] are attached. m is 2, 3 or 4.

Each of R[4] and R[5] is the same or different from each other and can be a hydrogen atom, a linear or branched chain alkyl group having 1 to 8 carbon atoms (e.g., methyl, ethyl, propyl, isopropyl, butyl, isobutyl, or tertbutyl), an alkenyl group having 2 to 8 carbon atoms (e.g., vinyl, allyl or 3-methyl-2-butenyl), an alkynyl group having 2 to 8 carbon atoms (e.g., propynyl), an aralkyl group having an alkylene moiety of 1 to 4 carbon atoms (e.g., benzyl or phenethyl), an aryl group (e.g., phenyl or naphthyl), a hydroxyl group, an alkoxy group having 1 to 8 carbon atoms (e.g., methoxy, ethoxy or propoxy), an aryloxy group (e.g., phenyloxy), an aralkyloxy group having an alkylene moiety of 1 to 4 carbon atoms (e.g., benzyloxy or phenethyloxy), a halogen atom (e.g., fluorine, chlorine or bromine), a nitro group, a cyano group, an alkylsulfonyl group having an alkyl moiety of 1 to 8 carbon atoms (e.g., methylsulfonyl), an arylsulfonyl group (e.g., benzenesulfonyl), an alkylcarbonyl group having an alkyl moiety of 1 to 8 carbon atoms (e.g., acetyl or propionyl), an arylcarbonyl group (e.g., benzoyl), an aralkylcarbonyl group (e.g., benzylcarbonyl), a halo-alkyl group having 1 to 8 carbon atoms and 1 to 3 halogen atoms such as chlorine, fluorine or bromine (e.g., chloromethyl, chloroethyl, or trifluoromethyl), a halo-alkoxy group having 1 to 8 carbon atoms and 1 to 3 halogen atoms such as chlorine, fluorine or bromine (e.g., 2-chloroethoxy or trifluoromethoxy), or a group represented by —NR[8]R[9] or —SO$_2$NR[10]R[11].

In the above-mentioned formula, each of R[8] and R[9] is the same or different from each other and can be a hydrogen atom, a linear or branched chain alkyl group having 1 to 8 carbon atoms (e.g., methyl, ethyl, propyl, isopropyl, butyl, or isobutyl), an aralkyl group having an alkylene moiety of 1 to 4 carbon atoms (e.g., benzyl or phenethyl) or an aryl group (e.g., phenyl or naphthyl).

Each of R[10] and R[11] is the same or different from each other and can be a hydrogen atom, a linear or branched chain alkyl group having 1 to 8 carbon atoms (e.g., methyl, ethyl, propyl, isopropyl, butyl, or isobutyl), an aralkyl group having an alkylene moiety of 1 to 4 carbon atoms (e.g., benzyl or phenethyl) or an aryl group (e.g., phenyl or naphthyl).

The dihydrophenazinecarboxylic acid derivative of the formula (III) is described in more detail.

R[21] of the formula (III) has the same meaning as that of R[1] of the formula (I), and each of R[22] and R[23] of the formula (III) has the same meaning as that of each of $R^2$ and $R^3$ of the formula (I), respectively. Each of $R^{26}$ and $R^{27}$ of the formula (III) [formula (IV)] has the same meaning as that of each of $R^6$ and $R^7$ of the formula (I) [formula (II)], respectively. Each of $R^{28}$ and $R^{29}$ of the formula (III) has the same meaning as that of each of $R^8$ and $R^9$ of the formula (I), respectively, and each of $R^{30}$ and $R^{31}$ of the formula (III) has the same meaning as that of each of $R^{10}$ and $R^{11}$ of the formula (I), respectively. Each of $R^{20}$, $R^{24}$ and $R^{25}$ of the formula (III) has the same meaning as that of $R^4$ or $R^5$ of the formula (I), under the condition that the alkylcarbonyl group, arylcarbonyl group, and aralkylcarbonyl group are excluded.

The dihydrophenazinecarboxylic acid derivative of the formula (V) is described in more detail.

$R^{41}$ of the formula (V) has the same meaning as that of $R^1$ of the formula (I), and each of $R^{42}$ and $R^{43}$ of the formula (V) has the same meaning as that of each of $R^2$ and $R^3$ of the formula (I), respectively. Each of $R^{44}$ and $R^{45}$ of the formula (V) has the same meaning as that of $R^4$ or $R^5$ of the formula (I) or can be a carboxy group or an alkoxycarbonyl group having 2 to 8 carbon atoms (e.g., methoxycarbonyl, or ethoxycarbonyl), an aralkyloxycarbonyl group (e.g., benzyloxycarbonyl), or a formyl group.

Each of $R^{46}$ and $R^{47}$ of the formula (V) [formula (VI)] has the same meaning as that of each of $R^6$ and $R^7$ of the formula (I) [formula (II)], respectively. Each of $R^{48}$ and $R^{49}$ of the formula (V) has the same meaning as that of each of $R^8$ and $R^9$ of the formula (I), respectively, and each of $R^{50}$ and $R^51$ of the formula (V) has the same meaning as that of each of $R^{10}$ and $R^{11}$ of the formula (I), respectively.

It should be noted that each of $R^4$ and $R^5$ of the formula (I), each of $R^{20}$, $R^{24}$ and $R^{25}$ of the formula (III), and each of $R^{44}$ and $R^{45}$ of the formula (V) can be single or plural.

The present inventors have found that a dihydrophenazinecarboxylic acid derivative of the formula (I) in which both of $R^4$ and $R^5$ are hydrogen atoms is easily oxidized under atmospheric conditions and is therefore unstable. For instance, the inventors have ascertained that ethyl 5,10-dihydro-1-phenazinecarboxylate is unstable at room temperature.

For the above-mentioned reason, each of $R^4$ and $R^5$ of the formula (I) and each of $R^{44}$ and $R^{45}$ of the formula (V) preferably is an electron-attracting group such as nitro or benzoyl.

The aromatic rings contained in the aralkyl group, aryl group, aryloxy group, aralkyloxy group, arylsulfonyl group, arylcarbonyl group, aralkylcarbonyl group, and aralkyloxy group of the substituent groups of the formulas (I), (III) and (V) can have substituent groups. The aromatic rings can be contained in the following groups:

aralkyl and aryl groups of $R^1$, $R^2$, $R^3$, $R^6$, $R^7$, $R^8$, $R^9$, $R^{10}$ and $R^{11}$ of the formula (I);

aralkyl, aryl, aryloxy, aralkyloxy, arylsulfonyl, arylcarbonyl and aralkylcarbonyl groups of $R^4$ and $R^5$ of the formula (I);

aralkyl and aryl groups of $R^{21}$, $R^{22}$, $R^{23}$ $R^{26}$, $R^{27}$, $R^{28}$ $R^{29}$, $R^{30}$ and $R^{31}$ of the formula (III);

aralkyl, aryl, aryloxy, aralkyloxy and arylsulfonyl groups of $R^{20}$, $R^{24}$ and $R^{25}$ of the formula (III);

aralkyl and aryl groups of $R^{41}$, $R^{42}$, $R^{43}$, $R^{46}$, $R^{47}$ $R^{48}$ $R^{49}$, $R^{50}$ and $R^{51}$ of the formula (V); and aralkyl, aryl, aryloxy, aralkyloxy, arylsulfonyl, arylcarbonyl, aralkylcarbonyl and aralkyloxycarbonyl groups of $R^{44}$ and $R^{45}$ of the formula (V).

Examples of the substituent groups which can be attached to the aromatic rings include a lower alkyl group having 1 to 6 carbon atoms (e.g., methyl, ethyl, or propyl), a lower alkoxy group having 1 to 6 carbon atoms (e.g., methoxy, ethoxy, or propoxy), a halogen atom (e.g., chlorine or fluorine), a lower alkyl group having 1 to 6 carbon atoms and 1 to 3 halogen atoms (e.g., trifluoromethyl), and a lower alkoxy group having 1 to 6 carbon atoms and 1 to 3 halogen atoms (e.g., trifluoromethoxy).

The linear or branched chain alkyl groups for $R^1$ of the formula (I), $R^{21}$ of the formula (III) and $R^{41}$ of the formula (V) can contain an amino group ($NH_2$), an alkylamino group having 1 to 6 carbon atoms (e.g., ethylamino), an aralkylamino having an alkyl moiety of 1 to 4 carbon atoms (e.g., benzylamino), a dialkylamino group having two alkyl moieties (each alkyl has 1 to 6 carbon atoms) (e.g., dimethylamino or diethylamino), a cyclic amino group (e.g., piperidino or morpholino), and a diaralkylamino group having two aralkyl moieties (each alkyl has 1 to 4 carbon atoms) (e.g., dibenzylamino).

The dihydrophenazinecarboxylic acid derivative of the formula (I) can be prepared by the following synthesis route:

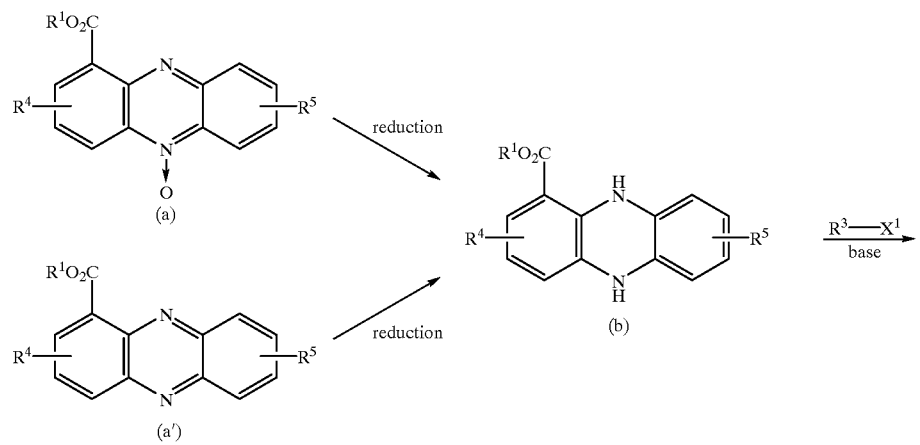

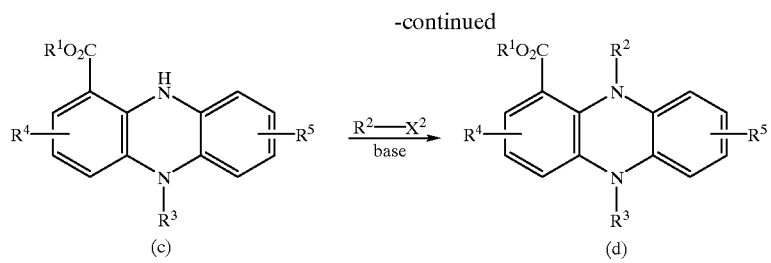

In the above-illustrated formulas, each of $X^1$ and $X^2$ represents a leaving group such as chlorine, bromine, iodine, mesyloxy, or tosyloxy; and each of $R^1$, $R^2$, $R^3$, $R^4$ and $R^5$ has the same meanings as mentioned hereinbefore, provided that there is no case where both of $R^2$ and $R^3$ are hydrogen atoms.

In the above-illustrated synthesis route, a compound of the formula (b) can be obtained by reducing a compound of the formula (a) or (a') in an inert solvent such as a mixture of ethanol and water at a temperature from room temperature to the boiling point of the solvent in the presence of a reducing agent such as sodium hydrosulfite.

When a compound of the formula (a') is employed as the starting compound, a compound of the formula (b) can be obtained by catalytic reduction using a Raney nickel catalyst, a palladium/carbon catalyst, or a rhodium catalyst in an inert solvent such as ethanol, methanol, acetone or methylene chloride. Otherwise, the compound of the formula (b) can be obtained by reducing the compound of the formula (a') by hydrazine and palladium/carbon in an inert solvent such as methanol or ethanol.

A compound of the formula (c) can be obtained by reacting the compound of the formula (b) with a compound of the formula $R^3X^1$ ($R^3$ and $X^1$ is the same as above) such as an alkyl halide in an inert solvent such as acetone, 2-butanone, 4-methyl-2-pentanone, or tetrahydrofuran in the presence of a base such as anhydrous potassium carbonate, anhydrous sodium carbonate, or sodium hydride.

A compound of the formula (d) can be obtained from the above-mentioned compound of the formula (b) in the same manner as described in the preparation of the compound of the formula (c).

The compound of the formula (b), (c) or (d) can be subjected to transesterification to give a different alkyl ester.

The starting compound of the formula (a) can be obtained in the same manner as that described, for instance, in J. Chem. Soc., Perkin Trans. 1, 1354(1974) or U.S. Pat. No. 3,615,494.

The compound of the formula (a') can be obtained in the same manner as that described, for instance, in J. Med. Chem., 30, 843(1987) or Synth. Commun., 17, 1171(1987).

The dihydrophenazinecarboxylic acid derivative of the formula (III) or (V) can be obtained in the same manner as that described above for the above-mentioned preparation of the dihydrophenazinecarboxylic acid derivative of the formula (I).

The dihydrophenazinecarboxylic acid derivative of the formula (I), (III), or (V) can be employed in the form of a pharmacologically acceptable salt with a base such as an alkali metal (e.g., sodium or potassium) or an organic amine (e.g., methylamine) or with an acid such as a mineral acid (e.g., hydrochloric acid or hydrobromic acid) or an organic acid (e.g., fumaric acid or acetic acid).

Representative examples of the dihydrophenazinecarboxylic acid derivatives of the formula (III) are set forth in Tables 1 and 2, in which "Position" means the position of benzoyl substituent.

TABLE 1

| $R^{21}$ | $R^{22}$ | $R^{23}$ | $R^{24}$ | $R^{25}$ | Position | $R^{20}$ |
|---|---|---|---|---|---|---|
| Et | H | H | H | H | 7 | H |
| H | H | 3-Me-2-Bute | H | H | 7 | H |
| Me | H | 3-Me-2-Bute | H | H | 7 | H |
| Et | H | 3-Me-2-Bute | H | H | 7 | H |
| i-Pr | H | 3-Me-2-Bute | H | H | 7 | H |
| t-Bu | H | 3-Me-2-Bute | H | H | 7 | H |
| Benz | H | 3-Me-2-Bute | H | H | 7 | H |
| Et | H | 3-Me-2-Bute | H | H | 7 | 3-NO$_2$ |
| Benz | H | 3-Me-2-Bute | H | H | 8 | 3-F |
| Et | H | Me | H | H | 7 | H |
| Et | H | Me | H | H | 7 | 3-F |
| Et | H | Me | H | H | 7 | 4-Cl |
| t-Bu | H | Me | H | H | 7 | 4-MeO |
| Et | H | Me | H | H | 7 | 3,4-diMeO |
| Et | H | Me | H | H | 9 | 4-Cl |
| Et | H | i-Bu | H | H | 6 | 4-F |
| Et | H | Benz | H | H | 7 | H |
| Et | H | 3-(diMeAm)Pr | H | H | 7 | H |

TABLE 2

| $R^{21}$ | $R^{22}$ | $R^{23}$ | $R^{24}$ | $R^{25}$ | Position | $R^{20}$ |
|---|---|---|---|---|---|---|
| Et | H | 2-(1-Pyrro)Et | H | H | 8 | H |
| Et | 3-Me-2-Bute | 3-Me-2-Bute | H | H | 7 | H |
| Et | Me | 3-Me-2-Bute | H | H | 7 | H |
| Et | Me | Benz | H | H | 7 | H |
| i-Bu | Benz | 3-Me-2-Bute | H | H | 7 | 4-Cl |
| Et | H | 3-Me-2-Bute | 3-Cl | H | 7 | H |
| Et | H | 3-Me-2-Bute | 4-Cl | H | 7 | H |
| Et | H | Benz | 3-Me | H | 7 | 3-NO$_2$ |
| Et | H | Benz | 2,3-diMeO | H | 7 | H |
| t-Bu | H | Me | H | 8-NO$_2$ | 7 | H |
| Benz | H | 3-Me-2-Bute | 4-MeO | 8-Cl | 7 | H |
| Et | H | Benz | H | 9-MeO | 7 | H |

TABLE 2-continued

| $R^{21}$ | $R^{22}$ | $R^{23}$ | $R^{24}$ | $R^{25}$ | Position | $R^{20}$ |
|---|---|---|---|---|---|---|
| Et | H | 3-Me-2-Bute | H | 9-(3-Me—) | 7 | H |
| 2-(diEtAm)Et | H | H | H | H | 7 | H |
| 3-(diMeAm)Pr | H | H | H | H | 7 | H |
| 3-(diMeAm)Pr | H | 3-Me-2-Bute | H | H | 7 | H |
| 3-(1-Pipe)Pr | H | H | H | H | 7 | H |
| 3-(1-Pipe)Pr | H | Me | H | H | 7 | H |
| 3-(1-Mor)Pr | H | Benz | H | H | 7 | H |

Remarks:
Me = methyl, Et = ethyl, Pr = propyl, i-Pr = isopropyl, i-butyl = isobutyl, t-butyl = tert-butyl, benz = benzyl, 3-Me-2-Bute = 3-methyl-2-butenyl, $NO_2$ = nitro, MeO = methoxy, diMeO = dimethoxy, (diMeAm)Pr = (dimethylamino)propyl, 2-(1-Pyrro)Et = 2-(1-pyrrolidinyl)ethyl, 9-(3-Me—) = 9-(3-methyl-2-butenyl), (diEtAm)Et = (diethylamino)ethyl (diEtAm)Pr = (diethylamino)propyl 3-(1-Pipe)Pr = 3-(1-piperidinyl)propyl 3-(1-Mor)Pr = 3-(1-morpholinyl)propyl Representative examples of the dihydrophenazinecarboxylic acid derivatives of the formula (I) (other than those shown in Tables 1 and 2) are set forth in Tables 3 and 4.

TABLE 3

| $R^1$ | $R^2$ | $R^3$ | $R^4$ | $R^5$ |
|---|---|---|---|---|
| H | H | H | H | 7-acetyl |
| Et | H | H | H | 7-acetyl |
| Et | H | H | H | 7-Cl |
| Et | H | H | H | 7-trifluoromethyl |
| Et | H | H | H | 7-(N-Mesulfamoyl) |
| Et | H | H | H | 7-trifluoromethoxy |
| H | H | 3-Me-2-Bute | H | 7-Cl |
| Et | H | 3-Me-2-Bute | H | 7-Cl |
| Et | H | 3-Me-2-Bute | H | 6-MeO |
| Et | Me | 3-Me-2-Bute | H | 9-MeO |
| Et | H | 3-Me-2-Bute | H | 7-trifluoromethyl |
| Et | H | 3-Me-2-Bute | 3-Cl | H |
| Et | H | 3-Me-2-Bute | 4-Cl | H |
| Et | H | 3-Me-2-Bute | 4-Cl | 7-Cl |
| Et | H | 3-Me-2-Bute | H | 7,8-dichloro |
| i-Pr | H | 3-Me-2-Bute | H | 7-(N-Mesulfamoyl) |
| Et | H | Me | H | 8-methylsulfonyl |
| Et | H | Me | 2-Cl | H |
| Et | H | Me | 3-Me | H |
| Et | H | Me | 2,3-dimethoxy | H |
| t-Bu | H | Me | H | 7-trifluoromethoxy |
| t-Bu | H | Me | H | 7,8-dimethoxy |
| Benz | H | Me | H | 7-cyano |
| Et | 3-Me-2-bute | Me | H | 7-(N-Mesulfamoyl) |
| Benz | H | i-Bu | 2,3-dimethoxy | 7-trifluoromethyl |

TABLE 4

| $R^1$ | $R^2$ | $R^3$ | $R^4$ | $R^5$ |
|---|---|---|---|---|
| Et | Me | Benz | H | 8-dimethylamino |
| Et | H | Benz | H | 8-(N-Mesulfamoyl) |
| Et | H | 3-(diEtAm)Pr | H | 7-Cl |
| Et | H | 2-(1-Pyrro)Et | H | 7,8-dimethoxy |
| 2-(diEtAm)Et | H | H | H | 7-acetyl |
| 3-(diMeAm)Pr | H | H | H | 7-$NO_2$ |
| 3-(diMeAm)Pr | H | 3-Me-2-Bute | H | 7-Cl |
| 3-(1-Pipe)Pr | H | Me | H | 8-methylsulfonyl |
| 3-(1-Mor)Pr | H | Benz | H | 7-Br |

Remarks:
8-(N-Mesulfamoyl) = 8-(N-methylsulfamoyl)

Representative examples of the dihydrophenazinecarboxylic acid derivatives of the formula (V) (other than those shown in Tables 1 to 4) are set forth in Tables 5 and 6, in which the substituent group of —$CO_2R^{41}$ is placed in the 2-position.

TABLE 5

| $R^{41}$ | $R^{42}$ | $R^{43}$ | $R^{44}$ | $R^{45}$ |
|---|---|---|---|---|
| H | H | H | H | 7-benzoyl |
| H | H | H | H | 8-(N-Mesulfamoyl) |
| H | H | H | H | 7-trifluoromethyl |
| H | H | H | H | 7,8-dichloro |
| H | H | 3-Me-2-Bute | H | 7-benzoyl |
| Et | H | 3-Me-2-Bute | H | 7-benzoyl |
| Et | H | 3-Me-2-Bute | H | 8-(N-Mesulfamoyl) |
| t-Bu | Me | 3-Me-2-Bute | H | 9-MeO |
| t-Bu | Me | Me | 4-MeO | 7-benzoyl |

TABLE 6

| $R^{41}$ | $R^{42}$ | $R^{43}$ | $R^{44}$ | $R^{45}$ |
|---|---|---|---|---|
| Et | Benz | Benz | 4-MeO | 7,8-dichloro |
| Et | H | 3-(diEtAM)Pr | H | 7-trifluoromethyl |
| Et | H | 3-(1-Pipe)Pro | H | 8-methylsulfonyl |
| 2-(diEtAm)Et | H | H | H | 7-benzoyl |
| 3-(diMeAm)Pr | H | H | H | 7-$NO_2$ |
| 3-(diMeAm)Pr | H | 3-Me-2-Bute | H | 7-benzoyl |
| 3-(1-Pipe)Pr | H | Me | H | 9-$NO_2$ |
| 3-(1-Mor)Pr | H | Benz | H | 7-benzoyl |

The results of pharmacological tests are set forth below.

The dihydrophenazinecarboxylic acid derivatives of the formulas (I), (III) and (V) and their salts showed excellent cytoprotective action in the glutamic acid toxicity inhibition tests using neurocyte (N18-RE-105 cell) and first hippocampal cell (rat fetus origin) and the BSO toxicity inhibition tests using neurocyte (N18-RE-105 cell). See the below-mentioned Example 10.

The known compounds showing inhibition of glutamic acid toxicity were effective to inhibit death of neurocyte caused by light ischemia of brain and activate metabolism of brain. Accordingly, the dihydrophenazinecarboxylic acid derivatives of the formulas (I), (III), and (V) are also effective as therapeutic agents for cerebrovascular diseases such as cerebral infarction and cerebrovacular dementia.

Further, the dihydrophenazinecarboxylic acid derivatives of the formulas (I), (III) and (V) and their salts showed excellent inhibition of peroxidation of lipid in the tests for evaluation of peroxidation inhibitory action using rat whole brain homogenate, as is described by the below-mentioned Example 10.

Examples of diseases assumed to be caused by active oxygen include inflammation, articular rheumatism, and autoimmune disease. Therefore, the dihydrophenazinecarboxylic acid derivatives of the formulas (I), (III) and (V) are effective in treating these diseases.

The inhibitory agent for inhibition of the glutamic acid toxicity containing an effective amount of the dihydrophenazinecarboxylic acid derivatives of the formula (I), (III) and (V) can be administered in the form of an oral agent such as pellet, capsule and granule or a parantheral agent such as injection or depository. The inhibitory agent can contain conventionally employed additives such as excipents such as glucose and lactose, disintegrators such as starch and carboxymethylcellulose calcium (CMC-Ca), binders such as hydroxypropylcellulose (HPC) and polyvinyl pyrrolidone (PVP), lubricants such as talc and magnesium stearate, diluents, and dyes.

The dihydrophenazinecarboxylic acid derivative of the formula (I), (III) or (V) can be administered into an adult at the dosage of approximately 0.001 mg to 100 mg/day in the case of injection and at the dosage of approximately 0.01 mg to 1.0 g/day in the case of oral administration. The dosage can be varied depending upon age, conditions, and others of the patient.

The present invention is further described by the following examples.

REFERENCE EXAMPLE 1

(1) N-(4-Benzoyl-2-nitrophenyl)anthranilic acid

A mixture of anthranilic acid (1.37 g, 10 mmol.), 4-chloro-3-nitrobenzophenone (2.88 g, 11 mmol.), anhydrous potassium carbonate (powder, 2.77 g, 20 mmol.), copper (powder, 50 mg), and isoamyl alcohol (25 mL) was stirred and heated for one hour under reflux. The reaction mixture was cooled to room temperature, and stirred for 15 minutes after addition of water (30 mL) and ether (30 mL). The insoluble red-brown solid was collected by filtration and washed with water and ether. The red-brown solid mainly comprising a potassium salt of the desired compound was suspended in water (40 mL). To the suspension was added 2M hydrochloric acid until an aqueous portion of the suspension showed approximately pH 2. The suspension was vigorously stirred for one hour at room temperature. The deposited crystalline precipitate was collected by filtration and washed with several portions of water and ether. The washed precipitate was placed under reduced pressure at 60° C. for 3 hours to dryness. Thus, 2.34 g (65%) of the desired compound was obtained as a yellow-orange crystalline product.

$^1$H NMR (CD$_3$OD/CDCl$_3$=1/1) δ: 7.25 (1H, br), 7.53–7.80 (8H, m), 7.97 (1H, brd, J=8Hz), 8.12 (1H, br), 8.68 (1H, d, J=2Hz).

(2) N-acetyl-N-(4-benzoyl-2-nitrophenyl)anthranilic acid

The above-obtained compound (8.70 g, 24.0 mmol.) was suspended in pyridine (100 mL). The suspension was stirred at room temperature for one day after addition of acetic anhydride (12.3 g, 0.12 mol.). The suspension was placed under reduced pressure to distill the solvent off. Water was added to the residue. The resulting aqueous suspension was made acidic by 2M hydrochloric acid until the aqueous portion reached approximately pH 2. The deposited precipitate was stirred at room temperature to turn it to powder. The crystalline powder was collected by filtration and washed with water. The washed powder was placed under reduced pressure at 60° C. for 5 hours to dryness. Thus, 9.50 g (98%) of the desired compound was obtained as a pale yellow powder.

$^1$H NMR (CD$_3$OD/CDCl$_3$=2/1) δ: 1.98 (3H, s), 7.30 (1H, d, J=8Hz), 7.51–7.84 (8H, m), 7.94 (1H, dd, J=8, 2Hz), 8.23 (1H, dd, J=8, 1Hz), 8.33 (1H, d, J=2Hz).

(3) ethyl N-acetyl-N-(4-benzoyl-2-nitrophenyl)anthranilate

In gaseous nitrogen atmosphere, the above-obtained compound (10.1 g, 25.0 mmol.) was suspended in anhydrous methylene chloride (80 mL). To the suspension were added 4-dimethylaminopyridine (3.36 g, 27.5 mmol.) and anhydrous ethanol (1.82 mL, 31.2 mmol.). The resulting mixture was chilled with ice, and stirred at 5° C. for one hour and at room temperature for 16 hours, after addition of 1-ethyl-3-(3-dimethylaminopropyl)carbodiimide hydrochloride (5.27 g, 27.5 mol.). The reaction mixture was placed under reduced pressure to distill the solvent off. The residue was mixed with water and ethyl acetate, and the organic portion was taken out. The organic portion was then washed successively with 1M hydrochloric acid, saturated aqueous sodium hydrogencarbonate solution, and saturated aqueous sodium chloride solution. The washed organic portion was dried over anhydrous sodium sulfate and placed under reduced pressure to distill the solvent off. The residue was recrystallized from ethanol (180 mL) to give 8.88 g (82%) of the desired compound. Further, 0.31 g (3%) of a secondary crystalline product was obtained from the mother liqueur.

$^1$H NMR (CDCl$_3$) δ: 1.32 (3H, t, J=7Hz), 1.96 (3H, s), 4.40 (2H, q, J=7Hz), 7.18 (1H, d, J=8Hz), 7.48–7.58 (3H, m), 7.60–7.68 (3H, m), 7.77–7.82 (2H, m), 7.92 (1H, dd, J=8, 2Hz), 8.14 (1H, br d, J=8Hz), 8.32 (1H, d, J=2Hz). FAB-MS m/z 433 (MH$^+$)

(4) 7-benzoyl-1-ethoxycarbonylphenazine 5-oxide

The above-obtained compound (8.75 g, 20.2 mmol.) was dissolved in acetonitrile (2.0 L). In gaseous nitrogen atmosphere, to the solution was irradiated for 10 hours a light from a 400W high pressure mercury lamp through a Pyrex filter. The reaction mixture was placed under reduced pressure to distill the solvent off. The residue was purified by medium pressure column chromatography (chloroform, chloroform/methanol=100/1). The resulting product was dissolved in heated ethanol (20 mL). The solution was allowed to stand overnight at room temperature. The deposited crystalline product was collected by filtration and washed with ethanol and ether. The washed product was placed under reduced pressure to dryness, to give 4.18 g (55%) of the desired compound as a yellow crystalline product. mp: 136–139° C.

$^1$H NMR (CDCl$_3$) δ: 1.52 (3H, t, J=7Hz), 4.60 (2H, q, J=7Hz), 7.53–7.58 (2H, m), 7.68 (1H, m), 7.79 (1H, dd, J=9, 7Hz), 7.88–7.92 (2H, m), 8.19 (1H, dd, J=7, 1Hz), 8.31 (1H, dd, J=9, 2Hz), 8.38 (1H, d, J=9Hz), 8.80 (1H, dd, J=9, 1Hz), 8.99 (1H, d, J=1Hz). FAB-MS m/z 373 (MH$^+$) IR (KBr) vcm$^{-1}$: 1720, 1650, 1430, 1350, 1295, 1280, 1190, 1135, 725.

EXAMPLE 1

Ethyl 7-benzoyl-5,10-dihydro-1-phenazinecarboxylate

To a boiled ethanol solution (300 mL) of 7-benzoyl-1-ethoxycarbonylphenazine 5-oxide (4.00 g, 10.7 mmol. obtained in Reference Example 1) was dropwise added for a period of one hour an aqueous solution (150 mL) of 85% sodium hydrosulfate (8.86 g, 43.2 mol.) in gaseous nitrogen atmosphere. After the dropwise addition was complete, the reaction mixture was further heated under reflux for 10 minutes. The refluxed mixture was then cooled to room temperature. To the cooled mixture was added water (150 mL). Thus deposited crystalline product was collected by filtration and washed with water. The washed product was placed under reduced pressure at 40° C. for 16 hours in the presence of diphosphorus pentoxide to dryness. Thus, 3.10 g (81%) of the desired compound was obtained as a brown-violet crystalline product. mp: 175–177° C.

$^1$H NMR (CD$_3$OD/CDCl$_3$=1/1) δ: 1.37 (3H, t, J=7Hz), 4.29 (2H, q, J=7Hz), 6.10 (1H, d, J=8Hz), 6.12 (1H, dd, J=8,

1Hz), 6.34 (1H, dd, J=8, 8Hz), 6.54 (1H, d, J=2Hz), 6.83 (1H, dd, J=8, 2Hz), 6.95 (1H, dd, J=8, 1Hz), 7.43–7.49 (2H, m), 7.56 (1H, m), 7.64–7.68 (2H, m), 8.97 (1H, br s). IR (KBr) νm$^{-1}$: 3310, 1655, 1630, 1605, 1590, 1560, 1470, 1440, 1315, 1290, 1250, 1220, 1155, 1120, 1075, 1000, 740, 705.

EXAMPLE 2

Ethyl 7-benzoyl-5,10-dihydro-5-(3-methyl-2-butenyl)-1-phenazinecarboxylate

In a 2-butanone suspension (6 mL) of the compound (359 mg, 1.00 mmol.) obtained in Example 1 were placed anhydrous potassium carbonate (powder, 0.83 g, 6.0 mmol.) and 4-bromo-2-methyl-2-butene (0.44 g, 3.0 mmol). The resulting mixture was refluxed for 7 hours with vigorous stirring in gaseous nitrogen atmosphere. The reaction mixture was cooled to room temperature, and then mixed with water and ethyl acetate. The organic portion was taken out. The aqueous portion was extracted with ethyl acetate. The organic portions were combined and washed with saturated aqueous sodium chloride solution. The washed organic portion was dried over anhydrous sodium sulfate and placed under reduced pressure to distill the solvent off. The residue was treated by medium pressure column chromatography (chloroform/hexane=2/1) to give a crude product (337 mg). The crude product was recrystallized from hexane containing a small amount of ethyl acetate to give 221 mg (52%) of the desired compound as a needle crystalline product. mp: 107–108° C.

$^1$H NMR (CDCl$_3$) δ: 1.36 (3H, t, J=7Hz), 1.70 (3H, br s), 1.74 (3H, br s), 3.97 (2H, br d, J=5Hz), 4.30 (2H, q, J=7Hz), 5.06 (1H, m), 6.17 (1H, d, J=8Hz), 6.19 (1H, br d, J=8Hz), 6.46 (1H, dd, J=8, 8Hz), 6.72 (1H, br s), 6.96 (1H, dd, J=8, 2Hz), 7.08 (1H, dd, J=8, 1Hz), 7.40–7.46 (2H, m), 7.52 (1H, m), 7.67–7.71 (2H, m), 9.45 (1H, br s). FAB-MS m/z 426 (M$^+$) IR (KBr) νcm$^{-1}$: 3250, 1675, 1640, 1585, 1500, 1470, 1445, 1270, 1250, 1240, 1135, 735.

EXAMPLE 3

Ethyl 7-benzoyl-5,10-dihydro-5,10-bis(3-methyl-2-butenyl)-1-phenazinecarboxylate Anhydrous THF solution (1 mL) of the compound (43 mg, 0.10 mmol.) obtained in Example 2 was chilled with ice. To the chilled solution were added successively 60% sodium hydride (6 mg, 0.15 mmol.) and after 5 minutes 4-bromo-2-methyl-2-butene (18 μL, 0.15 mmol.) in gaseous nitrogen atmosphere. The reaction mixture was stirred at 5° C. for one hour and at room temperature for 40 minutes. The reaction mixture was mixed with 10% aqueous citric acid solution (1 mL) and water (10 mL). The resulting mixture was extracted with ethyl acetate. The extract was washed with saturated aqueous sodium hydrogen-carbonate solution and saturated aqueous sodium chloride solution, and dried over anhydrous sodium sulfate. The dried solution was placed under reduced pressure to distill the solvent off. The residue was purified by preparative thin layer chromatography (ethyl acetate/hexane=1/3) to give 50 mg (100%) of the desired compound as red oil.

$^1$H NMR (CDCl$_3$) δ: 1.38 (3H, t, J=7Hz), 1.63 (3H, d, J=1Hz), 1.64 (3H, br s), 1.69 (3H, br s), 1.72 (3H, d, J=1Hz), 4.05 (2H, br d, J=6Hz), 4.20 (2H, br d, J=5Hz), 4.33 (2H, q, J=7Hz), 5.09–5.19 (2H, m), 6.41 (1H, d, J=8Hz), 6.48 (1H, dd, J=8, 1Hz), 6.74 (1H, dd, J=8, 8Hz), 6.91 (1H, d, J=2Hz), 7.08 (1H, dd, J=8, 1Hz), 7.18 (1H, dd, J=8, 2Hz), 7.41–7.47 (2H, m), 7.53 (1H, m), 7.70–7.75 (2H, m).

EXAMPLE 4

Ethyl 7-benzoyl-5-benzyl-5,10-dihydro-1-phenazinecarboxylate

To 2-butanone solution (4 mL) of the compound (180 mg, 0.502 mmol.) obtained in Example 1 were added anhydrous potassium carbonate (powder, 415 mg, 3.0 mmol.) and benzyl bromide (257 mg, 1.5 mmol.). The mixture was refluxed for 10 hours under vigorous stirring in gaseous nitrogen atmosphere. The reaction mixture was cooled to room temperature and mixed with water and ethyl acetate. The organic portion was taken out. The aqueous portion was extracted with ethyl acetate. The organic portions were combined, washed with saturated aqueous sodium chloride solution, and dried over anhydrous sodium sulfate. The dried organic portion was placed under reduced pressure to distill the solvent off. The residue was purified by medium pressure column chromatography (chloroform/hexane=2/1), to give 141 mg (63%) of the desired compound as an orange crystalline product. mp: 134–136° C.

$^1$H NMR (CDCl$_3$) δ: 1.37 (3H, t, J=7Hz), 4.31 (2H, q, J=7Hz), 4.62 (2H, br s), 6.08 (1H, br d, J=8Hz), 6.22 (1H, d, J=8Hz), 6.35 (1H, dd, J=8, 8Hz), 6.62 (1H, br s), 6.99 (1H, dd, J=8, 2Hz), 7.09 (1H, dd, J=8, 1Hz), 7.25–7.38 (7H, m), 7.45 (1H, m), 7.56–7.61 (2H, m), 9.53 (1H, br, s). IR (KBr) νcm$^{-1}$: 3280, 1670, 1635, 1610, 1585, 1520, 1495, 1470, 1440, 1315, 1270, 1250, 1140, 750, 705.

EXAMPLE 5

Ethyl 7-benzoyl-5,10-dihydro-5-methyl-1-phenazinecarboxylate

To an acetone suspension (4 mL) of the compound (180 mg, 0.502 mmol.) obtained in Example 1 were added anhydrous potassium carbonate (powder, 415 mg, 3.0 mmol.) and methyl iodide (0.19 mL, 3.0 mmol.). The mixture was heated under reflux with vigorous stirring in gaseous nitrogen atmosphere. After 4 hours, methyl iodide (0.19 mL, 3.0 mmol.) was again added to the reaction mixture. The reaction mixture was refluxed further for 16 hours. The reaction mixture was cooled to room temperature and mixed with water and ethyl acetate. The organic portion was taken out. The aqueous portion was extracted with ethyl acetate. The organic portions were combined, washed with saturated aqueous sodium chloride solution, and dried over anhydrous sodium sulfate. The dried organic portion was placed under reduced pressure to distill the solvent off. The residue was purified by medium pressure column chromatography (chloroform/hexane=2/1), to give 50 mg (27%) of the desired compound as an orange crystalline product. mp; 139–141° C.

$^1$H NMR (CDCl$_3$) δ: 1.37 (3H, t, J=7Hz), 2.94 (3H, s), 4.31 (2H, q, J=7Hz), 6.20 (1H, d, J=8Hz), 6.28 (1H, br d, J=8Hz), 6.53 (1H, dd, J=8, 8Hz), 6.85 (1H, br s), 6.96 (1H, dd, J=8, 2Hz), 7.13 (1H, dd, J=8, 1Hz), 7.42–7.47 (2H, m), 7.53 (1H, m), 7.68–7.72 (2H, m), 9.49 (1H, br s). IR (KBr) νcm$^{-1}$: 3260, 1680, 1640, 1590, 1550, 1500, 1475, 1440, 1420, 1320, 1275, 1250, 1240, 1170, 1140, 750, 740, 710.

EXAMPLE 6

3-(Dimethylamino)-propyl 7-benzoyl-5,10-dihydro-1-phenazinecarboxylate (1) ethyl 7-benzoyl-1-phenazinecarboxylate To a methanol suspension (6 mL) of 7-benzoyl-1-ethoxycarbonylphenazine 5-oxide (56 mg, 0.15 mmol.) obtained in Reference Example 1 was dropwise added an aqueous solution (2 mL) of sodium hydrosulfite (85%, 131 mg, 0.64 mmol.). The mixture was stirred for one hour at room temperature, and extracted with ethyl acetate after addition of water. The extract was washed with water and saturated aqueous sodium chloride solution, and dried over anhydrous sodium sulfate. The dried solution was placed under reduced pressure to distill the solvent off. The residue was purified by preparative thin layer chromatography (ethyl acetate/hexane=1/1), to give the desired compound as a yellow crystalline product. mp: 115–116° C.

$^1$H NMR (CDCl$_3$) δ: 1.53 (3H, t, J=7Hz), 4.62 (2H, q, J=7Hz), 7.53–7.59 (2H, m), 7.67 (1H, m), 7.89 (1H, dd, J=9, 7Hz), 7.91–7.96 (2H, m), 8.27 (1H, dd, J=7, 1Hz), 8.34 (1H, dd, J=9, 2Hz), 8.37 (1H, dd, J=9, 1Hz), 8.44 (1H, d, J=9Hz), 8.60 (1H, d, J=2Hz).

(2) 7-benzoyl-1-phenazinecarboxylic acid

To an ethanolic suspension (0.8 mL) of ethyl 7-benzoyl-1-phenazinecarboxylate (36 mg, 0.10 mmol.) obtained above was added 1M aqueous sodium hydroxide solution (0.20 mL, 0.20 mmol.). The mixture was then stirred for 4 hours at room temperature. The reaction mixture was further stirred for 0.5 hour after addition water (2 mL) and 0.5M hydrochloric acid (1 mL). The deposited crystalline product was collected by filtration and washed with water. The washed product was placed under reduced pressure at 40° C. for 16 hours, to give 33 mg (100%) of the desired compound as a yellow crystalline product. mp: 236–237° C.

$^1$H NMR (CDCl$_3$) δ: 7.55–7.62 (2H, m), 7.70 (1H, m), 7.92–7.97 (2H, m), 8.09 (1H, dd, J=9, 7Hz), 8.42 (1H, d, J=9Hz), 8.48 (1H, dd, J=9, 1Hz), 8.55 (1H, dd, J=9, 1Hz), 8.70 (1H, d, J=1Hz), 9.06 (1H, dd, J=7, 1Hz). IR (KBr) vcm$^{-1}$: 3050, 1740, 1650, 1590, 1405, 1315, 1285, 1240, 1170, 855, 760, 735, 720, 705.

(3) 3-(dimethylamino)propyl 7-benzoyl-1-phenazinecarboxylate

In an anhydrous dichloromethane suspension (3 mL) of 7-benzoyl-1-phenazinecarboxylic acid (66 mg, 0.20 mmol.) obtained above were added 4-dimethylaminopyridine (27 mg, 0.22 mmol.) and 3-dimethylamino-1-propanol (28 μL, 0.24 mmol.). The mixture was chilled with ice. To the mixture was added 1-ethyl-3-(3-dimethylaminopropyl) carbodiimide hydrochloride (43 mg, 0.22 mmol.). The resulting mixture was stirred at 5° C. for one hour and at room temperature for 21 hours. The reaction mixture was concentrated, and the residue was diluted with ethyl acetate and 5% aqueous sodium hydrogencarbonate solution. The organic portion was taken out, washed with water and saturated aqueous sodium chloride solution, and dried over anhydrous sodium sulfate. The dried mixture was placed under reduced pressure to distill the solvent off. The residue was purified by preparative thin layer chromatography (chloroform/methanol=5/1), to give 73 mg (88%) of the desired compound as a pale yellow solid product.

$^1$H NMR (CDCl$_3$) δ: 2.10 (2H, m), 2.34 (6H, s), 2.63 (2H, br t, J=7Hz), 4.61 (2H, t, J=6Hz), 7.54–7.59 (2H, m), 7.67 (1H, m), 7.90 (1H, dd, J=9, 7Hz), 7.90–7.96 (2H, m), 8.28 (1H, dd, J=7, 1Hz), 8.35 (1H, dd, J=9, 2Hz), 8.38 (1H, dd, J=9, 1Hz), 8.44 (1H, d, J=9Hz), 8.60 (1H, d, J=2Hz).

(4) 3-(dimethylamino)propyl 7-benzoyl-5,10-dihydro-1-phenazinecarboxylate

The procedures of Example 1 were repeated using 3-(dimethylamino)propyl 7-benzoyl-1-phenazinecarboxylate (406 mg, 0.601 mmol) obtained above, to give the desired compound (350 mg, 86%).

$^1$H NMR (CDCl$_3$) δ: 1.90 (2H, m), 2.25 (6H, s), 2.41 (2H, t, J=7Hz), 4.29 (2H, t, J=7Hz), 5.14 (1H, s), 6.09 (1H, bd, J=7Hz), 6.12 (1H, d, J=8Hz), 6.36 (1H, dd, J=8, 7Hz), 6.61 (1H, d, J=1Hz), 6.90 (1H, dd, J=8, 2Hz), 7.01 (1H, dd, J=8, 1Hz), 7.42–7.69 (5H, m), 9.04 (s, 1H).

EXAMPLE 7

3-(1-Piperidinyl)-propyl 7-benzoyl-5,10-dihydro-1-phenazinecarboxylate (1) 3-(1-piperidinyl)propyl 7-benzoyl-1-phenazine carboxylate The procedures of Example 6(3) were repeated using 7-benzoyl-1-phenazinecarboxylic acid (700 mg, 2.13 mmol.) obtained in Example 6(2) and 3-(1-piperidinyl)-1-propanol (366 mg, 2.56 mmol.), to give the desired compound (665 mg, 69%).

$^1$H NMR (CDCl$_3$) δ: 1.43–1.63 (6H, m), 2.10 (2H, m), 2.46 (4H, bs), 2.61 (2H, t, J=7Hz), 4.60 (2H, t, J=7Hz), 7.54–7.69 (3H, m), 7.89 (1H, dd, J=9, 7Hz), 7.92–7.95 (2H, m), 8.27 (1H, dd, J=7, 1Hz), 8.35 (1H, dd, J=9, 2Hz), 8.38 (1H, dd, J=9, 1Hz), 8.44 (1H, d, J=9Hz), 8.60 (1H, d, J=2Hz).

(2) 3-(1-piperidinyl)propyl 7-benzoyl-5,10-dihydro-1-phenazinecarboxylate

The procedures of Example 1 were repeated using 3-(1-piperidinyl)propyl 7-benzoyl-1-phenazinecarboxylate (600 mg, 1.32 mmol.) obtained above, to give the desired compound (370 mg, 61%).

$^1$H NMR (CDCl$_3$) δ: 1.42–2.02 (10H, m), 2.10 (2H, m), 2.55 (4H, bs), 4.27 (2H, t, J=6Hz), 5.06 (1H, s), 6.07 (1H, bd, J=7Hz), 6.11 (1H, d, J=8Hz), 6.35 (1H, t, J=8Hz), 6.60 (1H, d, J=2Hz), 6.90 (1H, dd, J=2, 8Hz), 6.99 (1H, bd, J=8Hz), 7.41–7.69 (5H, m), 9.00 (1H, s).

EXAMPLE 8

3-(Dimethylamino)-propyl 7-benzoyl-5,10-dihydro-5-(3-methyl-2-butenyl)-1-phenazinecarboxylate In toluene (12 mL) was dissolved ethyl 7-benzoyl-5,10-dihydro-5-(3-methyl-2-butenyl)-1-phenazinecarboxylate (1.26 g, 2.95 mmol.) obtained in Example 2. To the mixture were further added 3-(dimethylamino)-1-propanol (3.50 mL, 29.5 mmol.) and tetra-n-butyl-1-isothiocyanate-3-hydroxydistannoxane (SCN(n-Bu)$_2$SnOSn(n-Bu)$_2$OH; 329 mg, 0.591 mmol.). The mixture was stirred at 100° C. for 24 hours in the stream of gaseous nitrogen. The mixture was further stirred at 100° C. for 24 hours, after addition of 3-(dimethylamino)-1-propanol (1.50 mL) and the above-mentioned tin compound (329 mg, 0.591 mmol.). The reaction mixture was cooled to room temperature and poured into saturated aqueous sodium hydrogencarbonate solution. The aqueous mixture was then extracted with ethyl acetate. The extract was washed with two portions of saturated aqueous sodium chloride solution and dried over anhydrous sodium sulfate. The dried extract was placed under reduced pressure to distill the solvent off. The residue was purified by medium pressure column chromatography (CHCl$_3$/methanol=1/0→95/5), to give the desired compound (142 mg, 10%).

$^1$H NMR (CDCl$_3$) δ: 1.70 (3H, bs), 1.75 (3H, bs), 1.91 (2H, m), 2.25 (6H, s), 2.41 (2H, t, J=7Hz), 3.97 (2H, bd, J=5Hz), 4.30 (2H, t, J=6Hz), 5.06 (1H, m), 6.17 (1H, d, J=8Hz), 6.19 (1H, bd, J=9Hz), 6.46 (1H, t, J=8Hz), 6.72 (1H, d, J=1Hz), 6.97 (1H, dd, J=1, 8Hz), 7.06 (1H, dd, J=1, 8Hz), 7.42–7.70 (5H, m), 9.44 (1H, s).

EXAMPLE 9

3-(Dimethylamino)propyl 7-benzoyl-5,10-dihydro-5-(3-methyl-2-butenyl)-1-phenazinecarboxylate hydrochloride To an ethanolic solution (2 mL) of 3-(dimethylamino) propyl 7-benzoyl-5,10-dihydro-5-(3-methyl-2-butenyl)-1-phenazinecarboxylate (135 mg, 0.279 mmol.) obtained in Example 8 was added hydrogen chloride/ether (1M solution, 0.42 mL). The mixture was stirred at room temperature for one hour. The reaction solution was placed under reduced pressure to concentrate it to dryness, to give the desired compound (135 mg, 93%) as a red-violet amorphous product.

$^1$H NMR (DMSO-$_6$) δ: 1.62 (3H, bs), 1.71 (3H, bs), 2.10 (2H, m), 2.78 (3H, s), 2.80 (3H, s), 3.18 (2H, m), 3.98 (2H, bd, J=5Hz), 4.29 (2H, t, J=6Hz), 5.00 (1H, m), 6.34 (1H, bd, J=8Hz), 6.50–6.58 (3H, m), 6.92 (1H, bd, J=8Hz), 7.06 (1H, bd, J=8Hz), 7.49–7.62 (5H, m), 9.27 (1H, s), 10.0 (1H, bs).

REFERENCE EXAMPLE 2

Ethyl 7-benzoyl-5,10-dihydro-5-methoxycarbonyl-1-phenazinecarboxylate

To an anhydrous THF solution (10 mL) of the compound (359 mg, 1.00 mmol.) obtained in Example 1 were successively added 60% sodium hydride (40 mg, 1.00 mmol.) and after 5 minutes ethyl chlorocarbonate (120 μL, 1.57 mmol.) under chilling with ice and in gaseous nitrogen atmosphere. The mixture was stirred at 5° C. for one hour and at room temperature for 20 hours. The reaction mixture was mixed with 1M hydrochloric acid (1 mL) and water (40 mL) and then extracted with ethyl acetate. The extract was washed with saturated aqueous sodium chloride solution and dried over anhydrous sodium sulfate. The dried extract was placed under reduced pressure to distill the solvent off. The residue was purified by medium pressure column chromatography (chloroform), to give 166 mg (40%) of the desired compound as a yellow crystalline product. mp: 112–115° C.

$^1$H NMR (CDCl$_3$) δ: 1.42 (3H, t, J=7Hz), 3.82 (3H, s), 4.39 (2H, q), 6.87 (1H, d), 6.96 (1H, dd, J=8, 8Hz), 7.46–7.60 (2H, m), 7.52–7.60 (2H, m), 7.66 (1H, dd, J=8, 2Hz), 7.77–7.82 (3H, m), 7.86 (1H, d, J=2Hz), 9.94 (1H, br s).

EXAMPLE 10

(1) Test for inhibition of glutamic acid toxicity to neurocyte

The test was carried out using hybridoma (N18-RE-105 cell) of mouse neuroblastoma and rat retinal neurocyte.

Neuron 2, 1547 (1989) and J. Pharmacol. Exp. Ther, 250, 1132 (1989) report that death of cell is caused owing to oxidative stress originating from disturbance of cystine uptake into cells when a high concentration of glutamic acid (1–10 mM) is added to hybridoma.

The dihydrophenazinecarboxylic acid derivatives of the invention were examined in the action to the glutamic acid-induced cell death. As control, ethyl 7-benzoyl-5,10-dihydro-5-methoxycarbonyl-1-phenazinecarboxylate having a structure analogous to the compound of the invention, and the known antioxidants (nicaraven and ebselen) were examined.

Hybridoma cells were plated at 6.25×10$^3$ cells/cm$^2$. on on 96 well microplate in Dalbecco's modified MEM containing 10% FBS (fetal bovine serum) and HAT (hypoxanthine 0.1 mM, aminopterin 40 nM, thymidine 0.14 mM, Sigma Chem., Co.). After 24 hours, 10 mM glutamic acid and the test compound were added to the culture medium. After the addition of glutamic acid, the culture was maintained for further 24 hours. Then, the activity of lactate dehydrogenase (LDH) contained in the cells and the medium was determined. The LDH releasing ratio was calculated using the below-mentioned equation to examine the glutamic acid toxicity.

LDH releasing ratio=[LDH activity in medium/(LDH activity in cells and LDH activity in medium)]×100

(2) Test for inhibition of BSO toxicity to neurocyte (neurocyte protective action against cytotoxicity accompanied by decrease of amount of intracellular glutathione)

Neuron 2, 1547 (1989) and Experimental Medicine, 11, 2412 (1993) suggest that cause of the cell death of neurocyte N18-RE-105 is explained by the fact that the uptake of cystine by way of cystine/glutamic acid exchanging system is disturbed to deplete intracellular glutathione, whereby the oxidative stress does not diminish.

In view of the above-mentioned suggestion, the cytotoxicity of D,L-butionine (S,R)-sulfoximine (BSO), which is a glutathione-synthase inhibitor, was studied.

The culture of neurocyte N18-RE-105, addition of the test compound, and determination of lactate dehydrogenase (LDH) were carried out in the manner as described in (1) above. BSO was added at the concentration of 500 μM.

(3) Test for inhibition of glutamic acid toxicity to hippocampal cells in primary culture 1) Preparation of hippocampal cells (from rat fetus in primary culture)

A pregnant rat (18 days pregnancy) was anesthetized by Pentobarbital sodium. Its abdomen was sterilized using 83% ethanol and treated to take its fetus out. The whole brain was taken out from the fetus under stereomicroscopical observation. From the brain, its hippocampal portion was taken out. The hippocampal portion was cut into small pieces using a knife. The procedures for taking the hippocampal portion out and cutting the portion into small pieces were performed in a Hanks buffer solution (4° C.) without Ca$^{2+}$ and Mg$^{2+}$. The pieces of hippocampus were treated with 0.25% trypsin/0.01% DNase I solution at 37° C. for 30 minutes. After the addition of dialyzed FBS at the concentration of 20%, the treated specimen was recovered by centrifugal separation and suspended in DMEM containing GMS-A obtained from GIBCO (S1 culture medium). The specimen was gently treated by a pipet to give a cell suspension. The cells were plated at 1.0×10$^5$ cells/cm$^2$ on 48-well multiplate pre-coated with poly-L-lysine. After 3 hours, dialyzed FBS was added to give a final concentration of 10%. The cells were cultured at 37° C. for 4 days in 5% CO$_2$ atmosphere.

2) Determination of activity (Lactate dehydrogenase (LDH) method)

The cytoprotective action of the test compound was determined by measuring activity of LDH released from the dead cells and activity of LDH in the living cells. The hippocampal cells were cultured for 4 days, and then cultured for 48 hours in S1 culture medium (FBS was not added) containing 1 mM glutamic acid and the test compound. After the culturing procedure was complete, the activity of lactate dehydrogenase was determined in the manner described in 1) above.

(4) Test for inhibition of production of peroxidized lipid in rat whole brain homogenate From the rat which had been fed with vitamin E deficient food for 11 weeks, a whole brain was taken out and frozen in liquid nitrogen. After the frozen whole brain was pulverized to give a powder, it was homogenized by Dounce type homogenizer. The homogenate was subjected to centrifugal separation at 180×g for 10 minuets, and the supernatant was recovered. The recovered supernatant was employed as the whole brain homogenate. The reaction of lipid peroxidation was initiated by stimulation using iron-ascorbic acid. The peroxidized lipid was quantitatively analyzed by the thiobarbituric acid (TBA) method. In more detail, 200 μL of the whole brain homogenate (protein content: 12.5 mg/mL), 50 μL of ADP (2 mg/mL), 50 μL of FeSO$_4$ (0.5 mM), 50 μL of ascorbic acid (12 mM), and 50 μL of the test compound were added to 100 μL of 0.2M Tris-HCl buffer solution. The mixture was incubated at 37° C. for one hour. After the incubation was complete, 50 μL of 0.5% butylhydroxytoluene/ethanol solution, 250 μL of 8.1% SDS (sodium dodecylsulfate) solution, 1,750 μL of 20% acetic acid, and 1,500 μL of 0.8% TBA solution were added to the incubated mixture. The resulting mixture was boiled for one hour. After the boiling was complete, the mixture was cooled and then subjected to centrifugal separation at 1,500×g for 10 minutes. The separated supernatant was subjected to measurement of absorbance at 535 nm.

The results of the above-mentioned pharmacological tests (1), (2), (3) and (4) are set forth in Table 7.

TABLE 7

| Test compound | N18-RE-105 Cell | | Hippo-campal cell | Rat whole brain homogenate |
| | Glutamic $EC_{50}$ (nM) | BSO $EC_{50}$ (nM) | Glutamic $EC_{25}$ (nM) | (Inhibition of lipid peroxid) |
| --- | --- | --- | --- | --- |
| Compound 1 | 3.3 | 6 | — | — |
| Compound 2 | 14.5 | 96.2 | 12 | 60.2 |
| Compound 3 | 40.7 | 72 | — | — |
| Compound 4 | 58 | 90 | — | — |
| Compound 5 | — | — | 57.5 | — |
| Comparative | >1,000 | >1,000 | — | — |
| Nicarven | >100 × $10^3$ | >100 × $10^3$ | — | — |
| Ebselen | 10.1 × $10^3$ | 7.5 × $10^3$ | — | — |

Remarks:
In Table 7, "Glutamic" and "BSO" mean "Glutamic acid toxicity" and "BSO toxicity", respectively. "Inhibition of lipid peroxid" means "Inhibition of lipid peroxidation" and the number means "% per control value ($10^{-4}$M)".
Compound 1: ethyl 7-benzoyl-5,10-dihydro-1-phenazinecarboxylate
Compound 2: ethyl 7-benzoyl-5,10-dihydro-5-(3-methyl-2-butenyl)-1-phenazinecarboxylate
Compound 3: ethyl 7-benzoyl-5-benzyl-5,10-dihydro-1-phenazinecarboxylate
Compound 4: ethyl 7-benzoyl-5,10-dihydro-5-methyl-1-phenazinecarboxylate
Compound 5: 3-(dimethylamino)propyl 7-benzoyl-5,10-dihydro-5-(3-methyl-2-butenyl)-1-phenazinecarboxylate hydrochloride
Comparative: ethyl 7-benzoyl-5,10-dihydro-5-methoxy-carbanyl-1-phenazinecarboxylate From the results of Table 7, it is confirmed that the compounds of the invention have excellent cytoprotective activity to inhibit glutamic acid toxicity in neurocyte (N18-RE-105 cell) and hippocampal cell from rat fetus in primary culture. It is further confirmed that the compound have excellent cytoprotective activity to BSO toxicity in the neurocyte (N18-RE-105 cell).

In contrast, the comparative compound and the known antioxidants such as nicarven and ebseen showed no cytoprotective action to the glutamic acid toxicity and BSD toxicity in the neurocyte.

Moreover, it is confirmed from the results of Table 7 that the compounds of the invention show excellent inhibition of lipid peroxidation in the test for evaluating inhibition of lipid peroxidation using rat whole brain homogenate.

EXAMPLE 11

Acute toxicity

The compound of the invention (ethyl 7-benzoyl-5,10-dihydro-1-phenazinecarboxylate obtained in Example 1) was administered to ddY strain male mice (weight: 23 to 27 g) in a dose of 5 mg by intravenous injection. No death was observed.

What is claimed is:

1. A dihydrophenazinecarboxylic acid derivative having the formula (I): in which

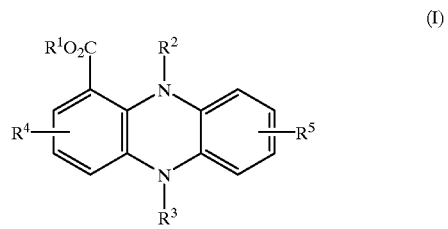

in which $R^1$ represents a hydrogen atom, a linear or branched chain alkyl group, an aralkyl group or an aryl group;

each of $R^2$ and $R^3$ is the same or different from each other and represents a hydrogen atom, an alkenyl group having 2 to 5 carbon atoms, an alkyl group, an aralkyl group, an aryl group, or a group represented by the formula (II):

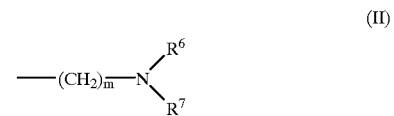

wherein each of $R^6$ and $R^7$ is the same or different from each other and represents a hydrogen atom, a linear or branched chain alkyl group, an aralkyl group or an aryl group, or $R^6$ and $R^7$ are combined together to form a nitrogen atom-containing 5- to 7-membered ring in conjunction with the adjacent nitrogen atom, and m is 2, 3 or 4;

each of $R^4$ and $R^5$ is the same or different from each other and represents a hydrogen atom, a linear or branched chain alkyl group, an alkenyl group, an alkynyl group, an aralkyl group, an aryl group, a hydroxyl group, an alkoxy group, an aryloxy group, an aralkyloxy group, a halogen atom, a nitro group, a cyano group, an alkylsulfonyl group, an arylsulfonyl group, an alkylcarbonyl group, an arylcarbonyl group, an aralkylcarbonyl group, a halo-alkyl group, a halo-alkoxy group, or a group represented by —$NR^8R^9$ or —$SO_2NR^{10}R^{11}$ wherein each of $R^8$ and $R^9$ is the same or different from each other and represents a hydrogen atom, a linear or branched chain alkyl group, an aralkyl group or an aryl group, and each $R^{10}$ and $R^{11}$ is the same or different from each other and represents a hydrogen atom, a linear or branched chain alkyl group, an aralkyl group or an aryl group; provided that at least one of $R^4$ and $R^5$ is a group selected from the group consisting of a nitro group, a cyano group, an alkylsulfonyl group, an arylsulfonyl group, an alkylcarbonyl group, an arylcarbonyl group, an aralkylcarbonyl group, a trifluoromethyl group, a trifluoromethoxy group, and a group represented by —$SO_2NR^{10}R^{11}$ wherein each of $R^{10}$ and $R^{11}$ is the same or different from each other and represents a hydrogen atom, a linear or branched chain alkyl group, an aralkyl group or an aryl group.

2. A method for treating a patient suffering from glutamic acid toxicity which comprises administering to the patient an effective amount of a dihydrophenazinecarboxylic acid derivative of the following formula (V):

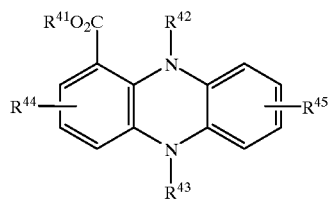

in which
R⁴¹ represents a hydrogen atom, a linear or branched chain alkyl group, an aralkyl group or an aryl group;

each of $R^{42}$ and $R^{43}$ is the same or different from each other and represents a hydrogen atom, an alkyl group, an aralkyl group, an aryl group, an alkenyl group having 2 to 5 carbon atoms, or a group represented by the formula (VI):

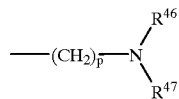

wherein each of $R^{46}$ and $R^{47}$ is the same or different from each other and represents a hydrogen atom, a linear or branched chain alkyl group, an aralkyl group or an aryl group, or $R^{46}$ and $R^{47}$ are combined together to form a nitrogen atom-containing 5- to 7-membered ring in conjunction with the adjacent nitrogen atom, and p is 2, 3 or 4;

each of $R^{44}$ and $R^{45}$ is the same or different from each other and represents a hydrogen atom, a linear or branched chain alkyl group, an alkenyl group, an alkynyl group, an aralkyl group, an aryl group, a hydroxyl group, an alkoxy group, an aryloxy group, an aralkyloxy group, a halogen atom, a nitro group, a cyano group, an alkylsulfonyl group, an arylsulfonyl group, an alkylcarbonyl group, an arylcarbonyl group, an aralkylcarbonyl group, a halo-alkyl group, a halo-alkoxy group, a carboxyl group, an alkoxycarbonyl group, an aralkyloxycarbonyl group, a formyl group, or a group represented by $-NR^{48}R^{49}$ or $-SO_2NR^{50}R^{51}$ wherein each of $R^{48}$ and $R^{49}$ is the same or different from each other and represents a hydrogen atom, a linear or branched chain alkyl group, an aralkyl group or an aryl group, and each of $R^{50}$ and $R^{51}$ is the same or different from each other and represents a hydrogen atom, a linear or branched chain alkyl group, an aralkyl group or an aryl group.

3. The method of claim 2, wherein at least one of $R^{44}$ and $R^{45}$ of the formula (V) is a group selected from the group consisting of a nitro group, a cyano group, an alkylsulfonyl group, an arylsulfonyl group, an alkylcarbonyl group, an arylcarbonyl group, an aralkylcarbonyl group, a trifluoromethyl group, a trifluoromethoxy group, and a group represented by $-SO_2NR^{50}R^{51}$, wherein each of $R^{50}$ and $R^{51}$ is the same or different from each other and represents a hydrogen atom, a linear or branched chain alkyl group, an aralkyl group or an aryl group.

4. An inhibitory agent of glutamic acid toxicity containing an effective amount of a dihydrophenazinecarboxylic acid derivative of the formula (I) set forth in claim 1.

5. A dihydrophenazinecarboxylic acid derivative having the formula (III):

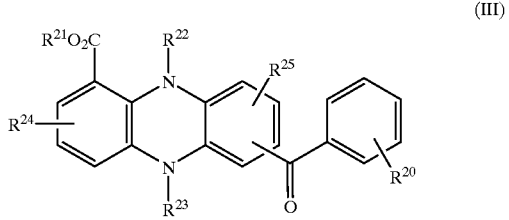

in which
$R^{21}$ represents a hydrogen atom, a linear or branched chain alkyl group, an aralkyl group or an aryl group;

each of $R^{22}$ and $R^{23}$ is the same or different from each other and represents a hydrogen atom, an alkenyl group having 2 to 5 carbon atoms, an alkyl group, an aralkyl group, an aryl group, or a group represented by the formula (IV):

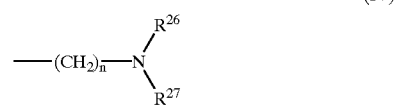

wherein each of $R^{26}$ and $R^{27}$ is the same or different from each other and represents a hydrogen atom, a linear or branched chain alkyl group, an aralkyl group or an aryl group, or $R^{26}$ and $R^{27}$ are combined together to form a nitrogen atom-containing 5- to 7-membered ring in conjunction with the adjacent nitrogen atom, and n is 2, 3 or 4;

each of $R^{20}$, $R^{24}$ and $R^{25}$ is the same or different from each other and represents a hydrogen atom, a linear or branched chain alkyl group, an alkenyl group, an alkynyl group, an aralkyl group, an aryl group, a hydroxyl group, an alkoxy group, an aryloxy group, an aralkyloxy group, a halogen atom, a nitro group, a cyano group, an alkylsulfonyl group, an arylsulfonyl group, a halo-alkyl group, a halo-alkoxy group, or a group represented by $-NR^{28}R^{29}$ or $-SO_2NR^{30}R^{31}$ wherein each of $R^{28}$ and $R^{29}$ is the same or different from each other and represents a hydrogen atom, a linear or branched chain alkyl group, an aralkyl group or an aryl group, and each of $R^{30}$ and $R^{31}$ is the same or different from each other and represents a hydrogen atom, a linear or branched chain alkyl group, an aralkyl group or an aryl group.

6. An inhibitory agent of glutamic acid toxicity containing an effective amount of a dihydrophenazinecarboxylic acid derivative of the formula (III) set forth in claim 5.

\* \* \* \* \*